(12) United States Patent
Overes et al.

(10) Patent No.: US 9,033,984 B2
(45) Date of Patent: May 19, 2015

(54) CLAVICLE NAIL WITH LATERAL EXPANDING AND ACTUATED PORTION

(75) Inventors: Tom Overes, Oberdorf (CH); Daniel Andermatt, Oberdorf (CH)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 195 days.

(21) Appl. No.: 13/407,144

(22) Filed: Feb. 28, 2012

(65) Prior Publication Data

US 2013/0158552 A1 Jun. 20, 2013

Related U.S. Application Data

(60) Provisional application No. 61/500,297, filed on Jun. 23, 2011, provisional application No. 61/537,860, filed on Sep. 22, 2011, provisional application No. 61/498,892, filed on Jun. 20, 2011.

(51) Int. Cl.
*A61B 17/56* (2006.01)
*A61F 2/30* (2006.01)
*A61B 17/58* (2006.01)
*A61B 17/72* (2006.01)
*A61B 17/17* (2006.01)

(52) U.S. Cl.
CPC ......... *A61B 17/7241* (2013.01); *A61B 17/1739* (2013.01); *A61B 17/7233* (2013.01); *A61B 17/7258* (2013.01)

(58) Field of Classification Search
CPC .......................................... A61B 17/72–17/748
USPC ............................................... 606/62–68, 313
See application file for complete search history.

(56) References Cited

U.S. PATENT DOCUMENTS

| | | | | |
|---|---|---|---|---|
| 3,678,925 | A * | 7/1972 | Fischer et al. | 606/68 |
| 3,760,802 | A * | 9/1973 | Fischer et al. | 606/63 |
| 4,227,518 | A * | 10/1980 | Aginsky | 606/63 |
| 5,057,103 | A * | 10/1991 | Davis | 606/63 |
| 5,441,500 | A * | 8/1995 | Seidel et al. | 606/67 |
| 5,713,903 | A * | 2/1998 | Sander et al. | 606/326 |
| 7,828,848 | B2 * | 11/2010 | Chauvin et al. | 623/17.16 |
| 8,337,495 | B1 * | 12/2012 | Powlan | 606/63 |
| 8,382,760 | B2 * | 2/2013 | Mantovani et al. | 606/63 |
| 2006/0155281 | A1 * | 7/2006 | Kaup et al. | 606/65 |
| 2007/0270954 | A1 * | 11/2007 | Wu | 623/17.11 |
| 2008/0287951 | A1 * | 11/2008 | Stoneburner et al. | 606/63 |
| 2009/0018542 | A1 * | 1/2009 | Saravia et al. | 606/63 |
| 2010/0023012 | A1 * | 1/2010 | Voor | 606/64 |
| 2011/0282346 | A1 * | 11/2011 | Pham et al. | 606/62 |
| 2012/0226326 | A1 * | 9/2012 | Overes et al. | 606/329 |

* cited by examiner

*Primary Examiner* — Mary Hoffman
*Assistant Examiner* — Michelle C Eckman
(74) *Attorney, Agent, or Firm* — Fay Kaplun & Marcin, LLP (57) ABSTRACT

A bone fixation nail having an elongated body configured and dimensioned for insertion into a bone. The elongated body has a first slot extending from the leading end to a first end and defining first and second wings, the first and second wings configured to splay radially outward upon application of an internal stress thereto.

20 Claims, 11 Drawing Sheets

CLAVICLE NAIL WITH LATERAL EXPANDING AND ACTUATED PORTION

PRIORITY CLAIM

The present application claims priority to U.S. Provisional Application Ser. No. 61/500,297 filed on Jun. 23, 2011 and entitled "Clavicle Nail With Lateral Expanding and Actuated Portion" and U.S. Provisional Application Ser. No. 61/537,860 filed on Sep. 22, 2011 and entitled "Clavicle Nail With Lateral Expanding and Actuated Portion" and U.S. Provisional Application Ser. No. 61/498,892 filed on Jun. 20, 2011 and entitled "Surgical Nail," the entire disclosures of which are incorporated herein by reference.

FIELD OF THE INVENTION

The present application is directed to the field of bone fixation and, more particularly, is directed to a bone fixation element configured for insertion into a fractured or otherwise damaged bone and subsequently locked thereto to lock a corrected position of the bone.

BACKGROUND INFORMATION

Systems and methods for the fixation of fractured or otherwise damaged bone sometimes require the insertion of a bone fixation device into a bone to, for example, bring fragments of the bone into a corrected alignment and/or increase a strength of the bone. Often, when subjected to wear after implantation, such a bone fixation device cannot maintain a sufficient holding force to prevent movement of the device within the bone. Thus, many of these bone fixation systems are subject to failure after implantation, reducing the efficacy of the bone fixation procedure and potentially leading to additional fractures.

SUMMARY OF THE INVENTION

In an aspect of the present invention, there is provided a bone fixation nail comprising an elongated body configured and dimensioned for insertion into a bone and a first slot extending through the elongated body from the leading end to a first end, the first slot defining first and second wings configured to splay radially outward upon application of an internal stress thereto.

In an exemplary embodiment, the first slot may have an internal thread provided on an inner wall of the elongated body and extending from the leading end of the elongated body to a second end. The elongated body may have a transverse opening formed adjacent a trailing end of the elongated body, the transverse opening defining an insertion axis extending at an angle to a longitudinal axis of the elongated body and configured to receive a bone fixation element therethrough.

In an other aspect of the present invention, there is provided a bone fixation nail comprising a transverse opening formed adjacent an end of the elongated body, the transverse opening defining an insertion axis extending at an angle to a longitudinal axis of the elongated body and configured to receive a bone fixation element therethrough.

In an exemplary embodiment, both leading and trailing ends of the nail body may comprise the transverse opening.

BRIEF DESCRIPTION OF THE DRAWINGS

Several embodiments of the invention will be described in the following by way of example and with reference to the accompanying drawings in which.

DETAILED DESCRIPTION

The present invention is directed to a system and method for bone fixation comprising a bone fixation device configured for insertion into a bone (e.g., into a medullary cavity). Specifically, the bone fixation device according to the invention is formed as an elongated nail attached at a distal end to an elongated expansion core, which is further attached to an elongated reamer configured for insertion into a selected location of a target bone (e.g., a medial or lateral end of bone such as a clavicle) and out of another location of the bone. The reamer is advanced through the bone until a trailing end of the bone fixation device lies substantially flush against an outer surface of the selected location of the bone. The reamer is then removed from the bone fixation device. The trailing end of the bone fixation device comprises a transverse screw hole configured to permit insertion of a locking screw therethrough at a desired angle, as will be described in greater detail later on. The leading end of the bone fixation device comprises a slot extending towards the trailing end, the slot defining first and second wings on lateral sides thereof. After insertion of the locking screw, the expansion core is rotated relative to the bone fixation device, the rotation causing the expansion core to move into the bone fixation device and subsequently cause the first and second wings to flare radially outward to increase a holding force of the bone fixation device within the bone. The exemplary device according to the invention is usable with both the right and left clavicle and for a wide range of anatomical lengths. It is noted that although the exemplary embodiment is disclosed with respect to a device configured for insertion into a clavicle, the exemplary system and method according to the invention may be employed in any other bone without deviating from the scope of the invention.

Figure 1:
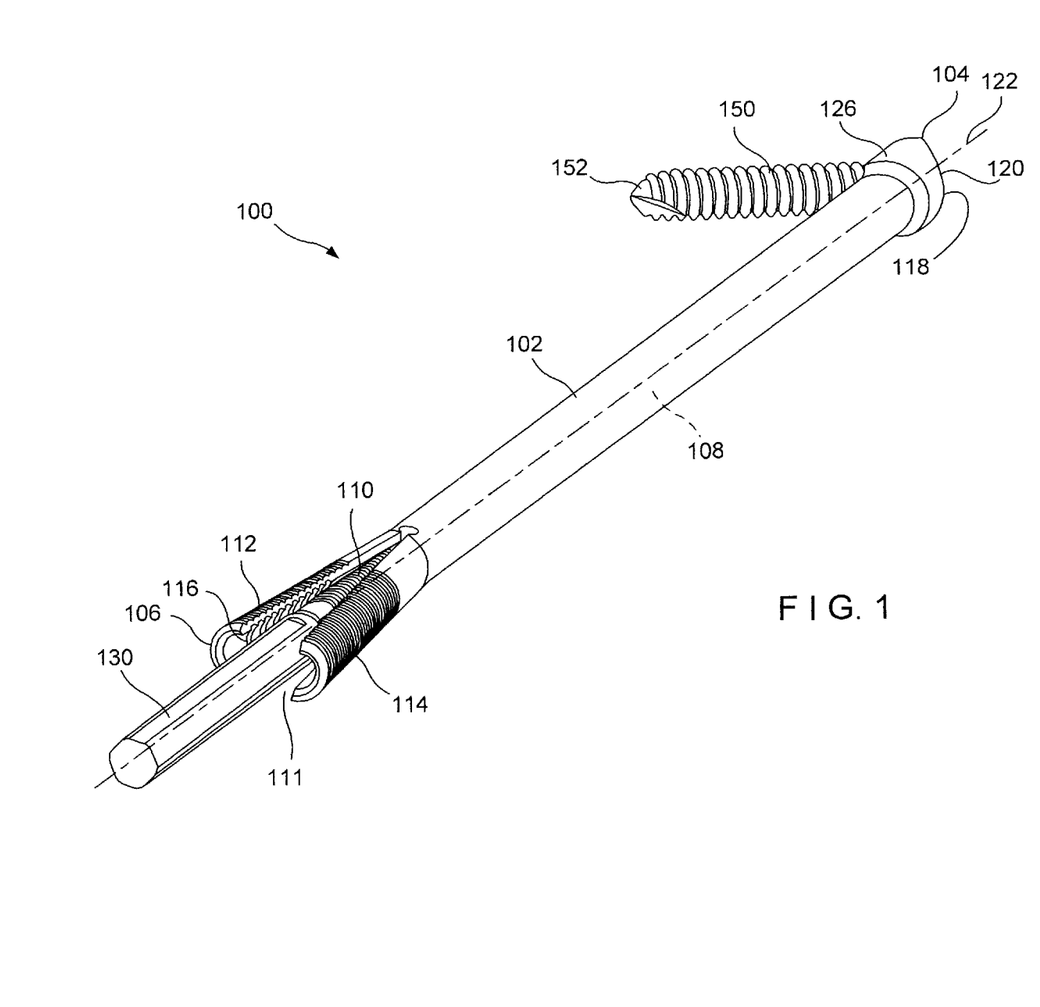
FIG. 1 illustrates a bone fixation device according to an exemplary embodiment of the invention.
Figure 2:
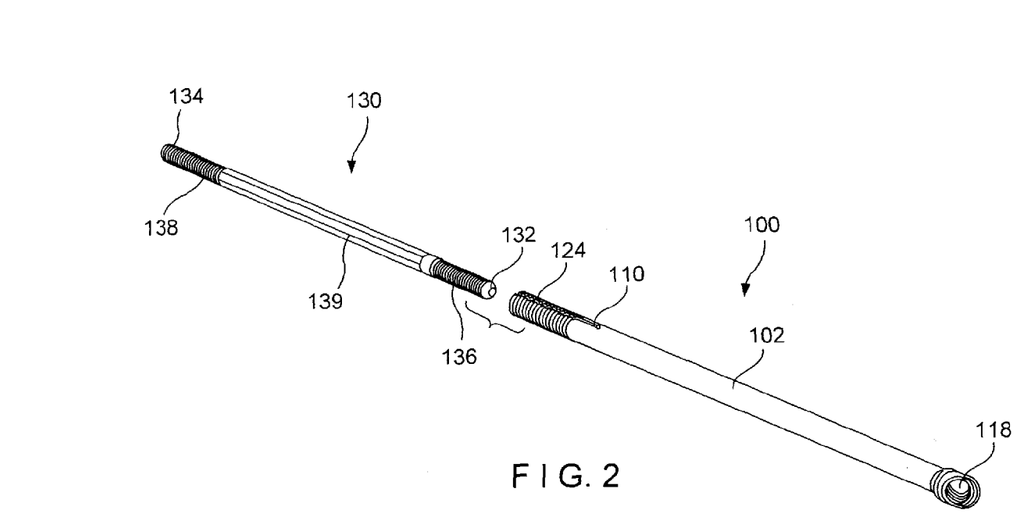
FIG. 2 illustrates the bone fixation device of claim 1 in a pre-operative configuration.
Figure 3:
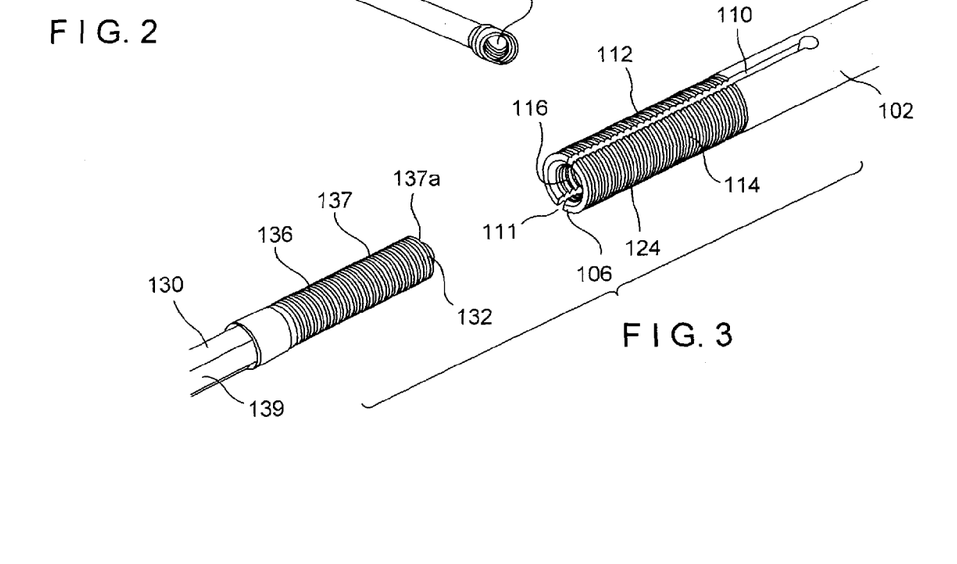
FIG. 3 illustrates a zoomed perspective view of the device of FIG. 2.
Figure 7A:
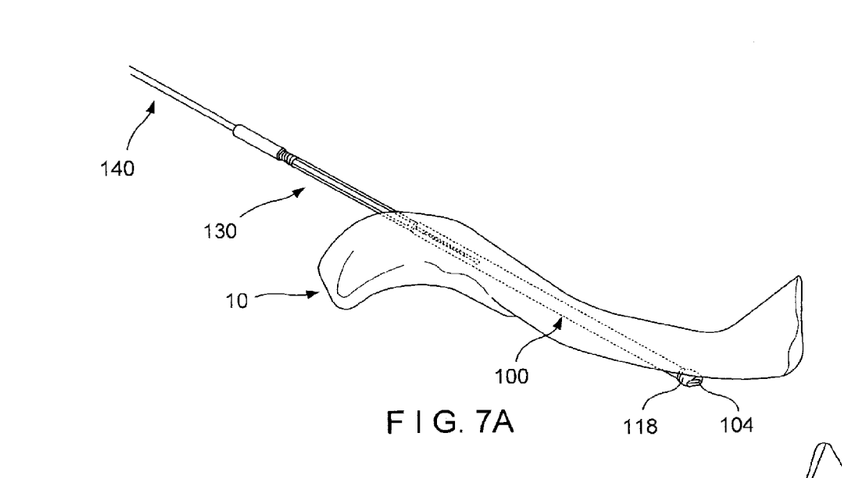
FIG. 7A illustrates a first perspective view of the bone fixation device of FIG. 1 in a second operative configuration.
Figure 7B:
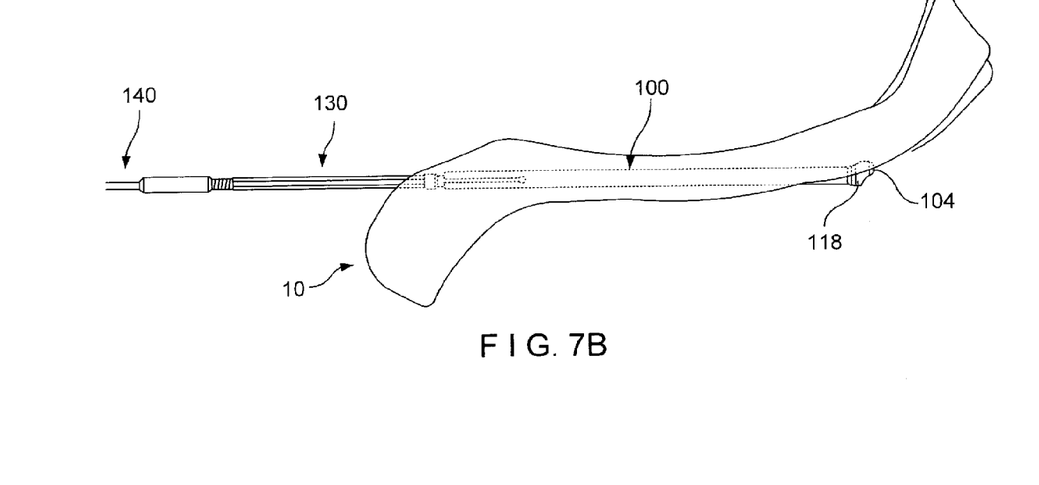
FIG. 7B illustrates a second perspective view of the bone fixation device of FIG. 1 in a second operative configuration.
Figure 8:
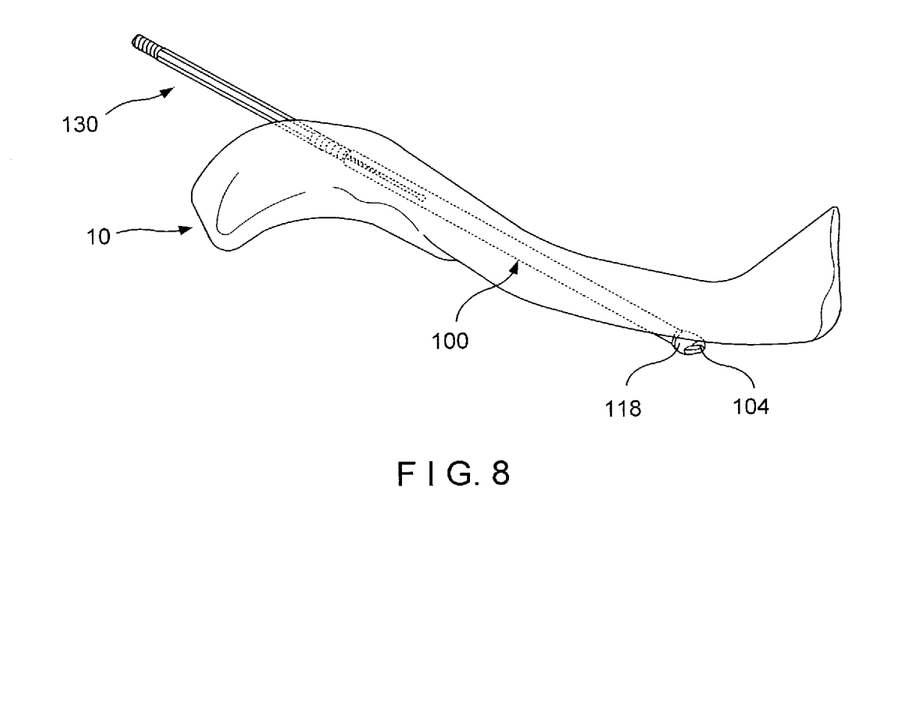
FIG. 8 illustrates the bone fixation device of FIG. 1 in a third operative configuration.

FIGS. 1-3 depict an exemplary bone fixation device 100 according to the present invention. The bone fixation device 100 comprises an elongated, substantially cylindrical body 102 extending from a trailing end 104 to a leading end 106. In an exemplary embodiment, a diameter of the cylindrical body is approximately 3.5 mm, although any other dimensions may be used without deviating from the scope of the invention. The leading end 106 of the device 100 comprises first and second slots 110, 111, respectively, extending a predetermined distance into the leading end 106. The first and second slots 110, 111 define first and second wings 112, 114 on opposite sides of the body 102. An inner wall of the leading end 106 may be provided with a female thread 116 configured to threadedly engage a male thread 136 of an expansion core 130 to be received therein, as will be described in greater detail later on. The female thread 116 extends a predetermined length into the leading end 106 to permit threaded insertion of the expansion core 130 into the device 100. A transverse opening 118 adjacent the trailing end 104 of the device 100 opens into an opening channel 120 having a channel axis 121 extending at an angle of approximately 45° relative to a longitudinal axis 122 of the device 100. In another embodiment, the opening channel 120 extends at an angle of approximately 30°-60° relative to the longitudinal axis 122. It is noted, however, that any other angle may be employed without deviating from the scope of invention. For example, the angle of the opening channel 120 may be selected so that, once implanted in a target portion of a clavicle 10, the opening channel 120 is substantially orthogonal to an axis of the clavicle. The angle may also be selected to avoid intersection with nerves or other sensitive structures lying adjacent to the clavicle, as would be understood by those skilled in the art. It is therefore submitted that any angle may be selected between the opening channel 120 and longitudinal axis 122 without deviating from the scope of the invention. In yet another embodiment (not shown), the transverse opening 118 may be a variable angle hole, permitting a user to select an angle of insertion of a bone fixation screw 150 inserted therethrough in accordance with the requirements of a particular medical procedure, as those skilled in the art will understand. A proximal face of the transverse opening 118 is angled so that, when implanted in the clavicle, the proximal face lies substantially flush against an outer surface of the clavicle as show in FIGS. 7A and 7B. An inner wall of the channel 120 includes a locking female thread configured to threadedly engage the locking bone fixation screw 150, as will be described in greater detail later on. The trailing end 104 also comprises an increased diameter portion 126 configured to limit the extent to which the device may move laterally or medially into the clavicle 10. In an exemplary embodiment, a diameter of the portion 126 may be approximately 1 mm. larger than outlying portions of the device 100 so that the trailing end 104 will engage bone around the opening preventing the device 100 from moving further distally thereinto.

As shown in FIG. 3, a gripping surface 124 is provided adjacent the leading end 106. The gripping surface 124 is defined by a ribbed outer wall and is configured to increase frictional interference with the clavicle 10 after implantation. It is noted that although a ribbed wall 124 is shown, any other surface-treated wall may be used without deviating from the scope of the present invention (e.g., a roughened surface, etc.).

The expansion core 130 is formed as an elongated rod extending from a first end 132 to a second end 134. The first end 132 comprises the male thread 136 configured to mate with the female thread 116 of the nail 100. The first end 132 has a tapered end region for ease of alignment and insertion of the proximal end into the female thread 116. first end 132 leading end 106 The first end 132 also comprises a reduced diameter portion (not shown) having an outer diameter substantially similar to a diameter of the female thread 116 to permit a thread start of the expansion core 130 to threadedly engage the female thread 116, as those skilled in the art will understand. The tapering of the first end 132 expands to the male thread 136. The male thread 136 has a substantially uniform cross-sectional diameter configured to mate with the female thread 116. The male thread 136 extends along the body to an expansion member 137. The expansion member 137 has a diameter just larger than the outer diameter of the male thread 136 and the inner diameter of the female thread 116. For example, if the male thread 136 is 2.5 mm in diameter, the expansion member 137 is 2.7 mm to 3.0 mm in diameter. The leading end region 137a of the expansion member 137 is tapered for ease of insertion and engagement of the expansion member 137 with the wings 112, 114. As one of skill in the art would understand, driving the expansion member 137 into the wings 112, 114 causes the expansion core 130 to move the first and second wings 112, 114 laterally away from one another. The second end 134 of the expansion core 130 comprises a threaded portion 138 configured to threadedly engage a reamer 140, as will be described in greater detail hereinafter. A body portion 139 of the expansion core 130 may be formed with a non-circular cross-sectional shape including a plurality of faceted walls, wherein the cross-sectional shape may be triangular, rectangular, pentagonal, hexagonal, etc. The threaded portion 138 may be milled over the faceted body portion 139. In an exemplary embodiment, a strength of the connection between the expansion core 130 and the reamer 140 is preferably strong enough to resist separation whilst the reamer is being used to pull the device 100 into a bone, such as a clavicle.

As one of skill in the art would understand, the male thread could have any configuration suitable for expanding the wings 112, 114. For example, the male thread 136 may be formed along a substantially conically tapered surface an outer diameter of which increases in a direction away from the first end 132 to a maximum diameter. Specifically, the maximum outer diameter of the portion along which the male thread 136 is formed may be larger than an inner diameter of the female thread 116 so that insertion of the portion including the male thread 136 proximally into the leading end 106 of the device 100 radially expands expansion core 130 by moving the first and second wings 112, 114 laterally away from one another.

Figure 4:
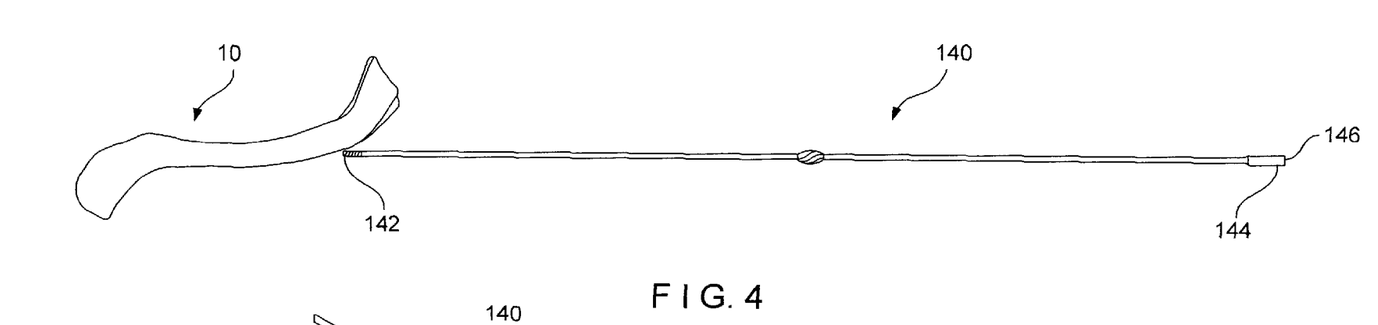
FIG. 4 illustrates a first perspective view of a reamer for use with the bone fixation device of FIG. 1.

FIG. 4 depicts an exemplary reamer 140 according to the invention. The reamer 140 is formed as an elongated instrument having a leading end 142 configured for insertion into the clavicle 10, as those skilled in the art will understand. For example, the reamer 140 has a sharpened tip (not shown) and is connected to a driving mechanism (not shown) to aid in insertion thereof into the clavicle 10, as will be described in greater detail later on. A trailing end 144 of the reamer comprises a threaded opening 146 configured to threadedly mate with the threaded portion 138 of the expansion core 130. The reamer 140 is dimensioned so that, when the leading end 142 is inserted through the clavicle 10 at a desired angle, the trailing end 144 remains proximal to the clavicle accessible to a physician or other user, as will be described in greater detail below in the description of an exemplary method according to the invention. In a device according to an exemplary embodiment of the invention, an outer diameter of the reamer 140 is approximately 4.5-5 mm. Diameters of the device 100 and the expansion core 130 may be selected to be the same as or slightly smaller than that of the reamer 140 preventing the reamer from being retracted into the expansion core 130 when attached thereto. In one embodiment of the invention, diameters of the expansion core and the device 100 are approximately 1 mm. smaller than the diameter of the reamer 140. In an exemplary embodiment, the diameters of the expansion core 130 and the device 100 are each approximately 3.5 mm.

Figure 5:
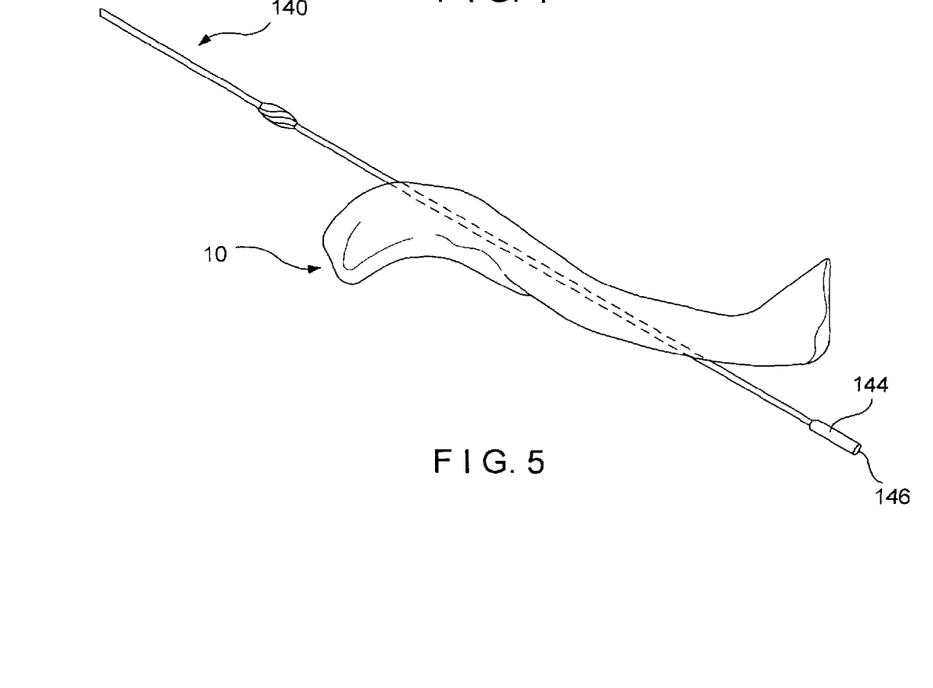
FIG. 5 illustrates a second perspective view of the reamer of FIG. 4.
Figure 6:
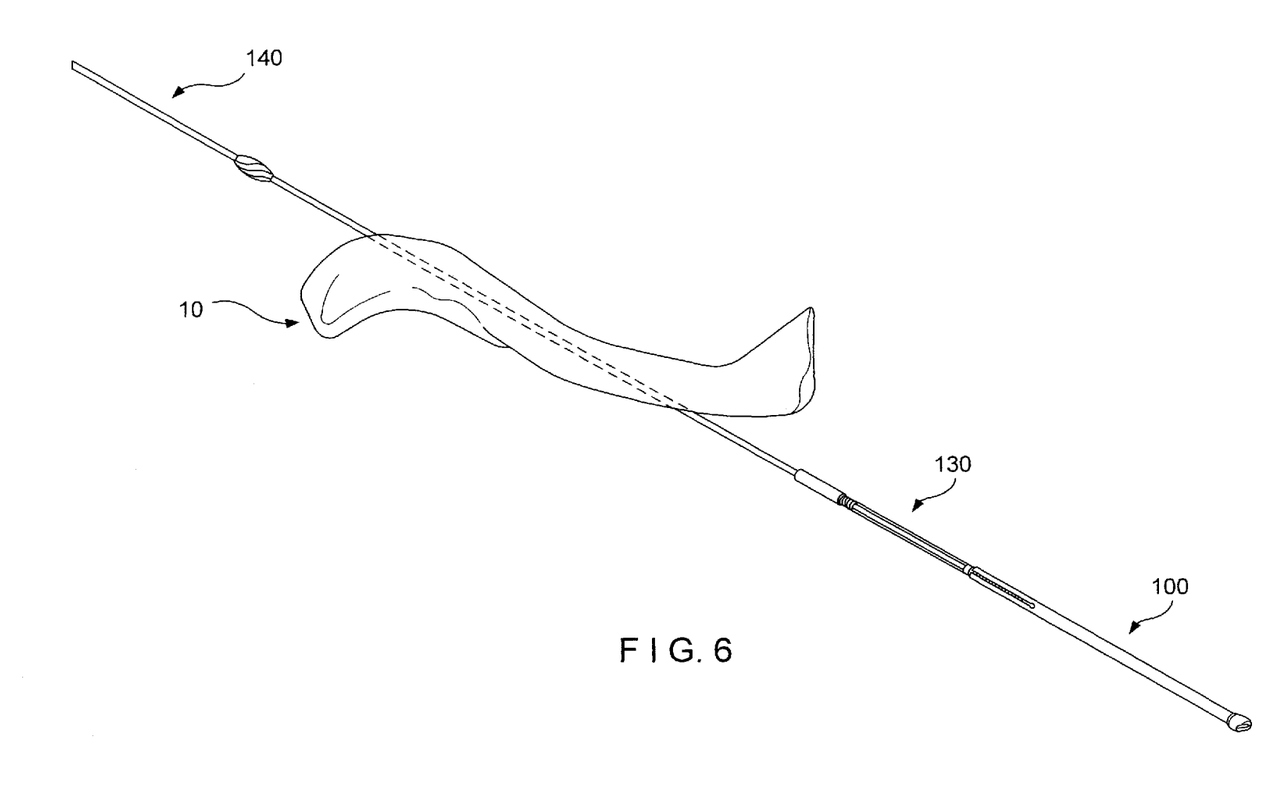
FIG. 6 illustrates a perspective view of the bone fixation device of FIG. 1 in a first operative configuration.

FIGS. 5-13 show an exemplary method of inserting and deploying the device 100. The method shown represent use of the device 100 where it is inserted in a medial to lateral insertion direction into a bone. However, as one of skill in the art would understand, the device could be inserted in any manner into a bone depending on the type of surgery required or according to the preference of a surgeon. For example, the device 100 could be inserted in a lateral to medial insertion direction. In accordance with the exemplary method, a physician or other user first determines a desired angle of insertion of the reamer 140 into the bone. In an exemplary embodiment, the device 100 is angled so the first and second slots 110, 111 lie in a supero-inferior direction to maximize radial deflection of the first and second wings 112, 114 upon actuation by the expansion core 130. It is noted, however, that any other desired angle of insertion may be employed without deviating from the scope of the invention. A first incision is made adjacent a medial portion of the clavicle 10 for the entry of the reamer 140 into the skin and a second lateral incision is made adjacent a lateral portion of the clavicle 10 to permit the reamer 140 to exit therefrom. A reverse reaming technique is used to insert the reamer 140 from a medial portion of the clavicle 10 and through the clavicle 10 at the desired angle until the leading end 142 exits a lateral wall of the clavicle 10, as shown in FIG. 5. Specifically, the trailing end 144 of the reamer 140 may be connected to the driving mechanism (not shown) during insertion through the clavicle 10 and disengaged therefrom once the reamer 140 has been positioned as shown in FIG. 5. The threaded portion 138 of the expansion core 130 is then threaded into the threaded opening 146 of the reamer and the device 100 is attached to the expansion core 130 by threading the male thread 136 into the female thread 116. The expansion member 137 acts as a marker for indicating a maximum depth of insertion of the male thread 136 into the female thread 116 prior to insertion thereof into the bone to, for example, prevent a premature expansion of the first and second wings 112, 114. The reamer 140 is then advanced further distally into the clavicle 10 until the device 100 has been pulled through a channel defined by the reamer 140. Specifically, the physician or other user may pull the leading end 142 of the reamer to advance the expansion core 130 and device 100 into the clavicle 10. In an exemplary embodiment, the device 100 is positioned so the transverse opening 118 at the trailing end 104 lies substantially flush against a medial cortex of the clavicle, as shown in FIGS. 7A and 7B. The reamer 140 is then unthreaded and removed from the expansion core 130. As those skilled in the art will understand, a compression tool (not shown) may optionally be used to provide additional compression during insertion of the expansion core 130.

Figure 9A:
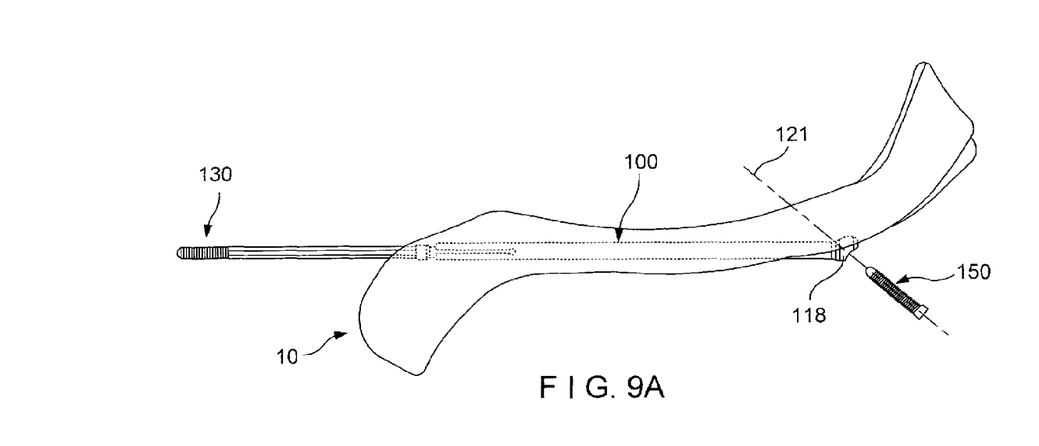
FIG. 9A illustrates the bone fixation device of FIG. 1 in a fourth operative configuration.
Figure 9B:
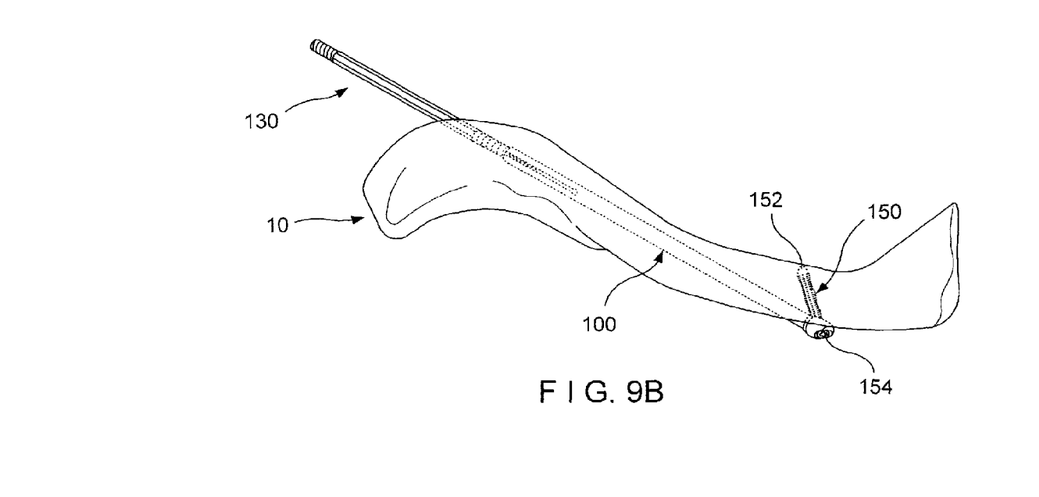
FIG. 9B illustrates a second perspective view of the bone fixation device of FIG. 1 in a fifth operative configuration.

As shown in FIGS. 9A and 9B, the locking screw 150 is then inserted into the transverse opening 118. The locking screw 150 may be a standard 2.7 mm bone screw although any other screw may be used without deviating from the scope of the invention. As would be understood by those skilled in the art, a length of the locking screw 150 is preferably selected so that, when inserted through the transverse opening 118, a distal end 152 engages with at least a portion of the cortical bone on a side of the bone opposed to the entry point into the transverse opening 118. As one of skill in the art will understand, the length of the screw chosen is decided by a user, such as a surgeon, and could depend on several factors included the size of a bone, desired result of an operation, etc. For example, the surgeon may choose a locking screw 150 such that a portion of the distal end 152 sticks out of the other side of the bone for ensuring that screw is sufficiently fixed to the bone. A head 154 of the locking screw 150 is seated flush with the transverse opening 118 against an outer surface of the clavicle 10. The locking screw 150 is formed with threading configured to engage threads of the transverse opening 118. In one embodiment of the invention, the channel 120 may be substantially conical to engage a respectively shaped locking screw 150. It is noted that the channel 120 and locking screw 150 may also be formed in any other shape without deviating from the scope of the invention (e.g., cylindrical, etc.).

Figure 10:
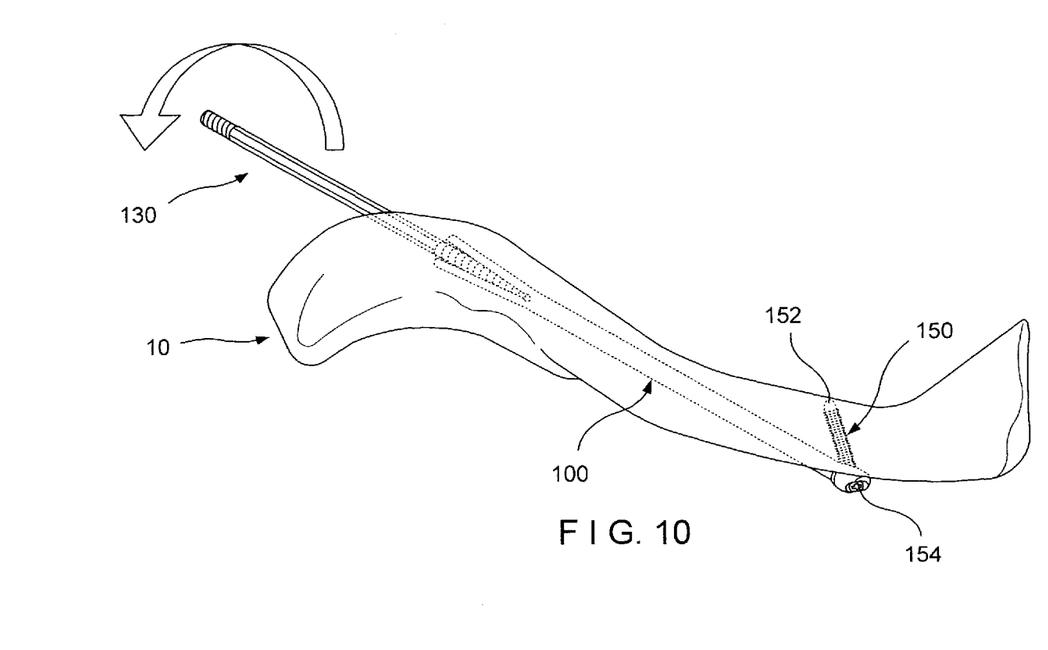
FIG. 10 illustrates the bone fixation device of FIG. 1 in a sixth operative configuration.
Figure 11:
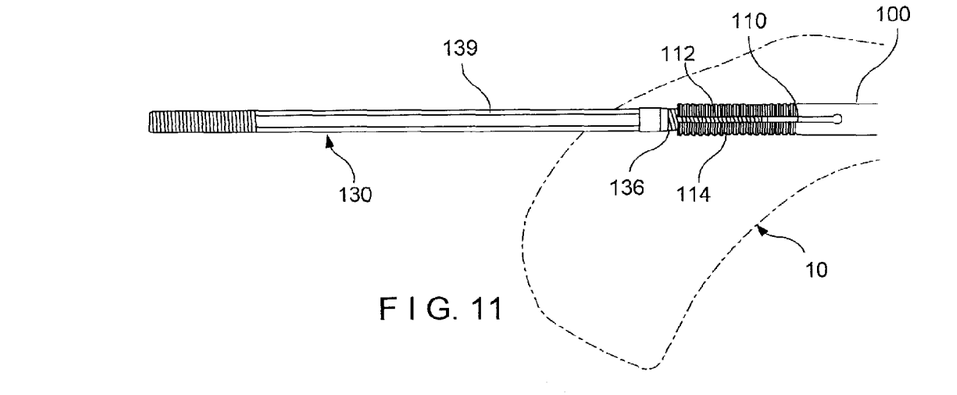
FIG. 11 illustrates the bone fixation device of FIG. 1 in the fifth operative configuration.
Figure 12:
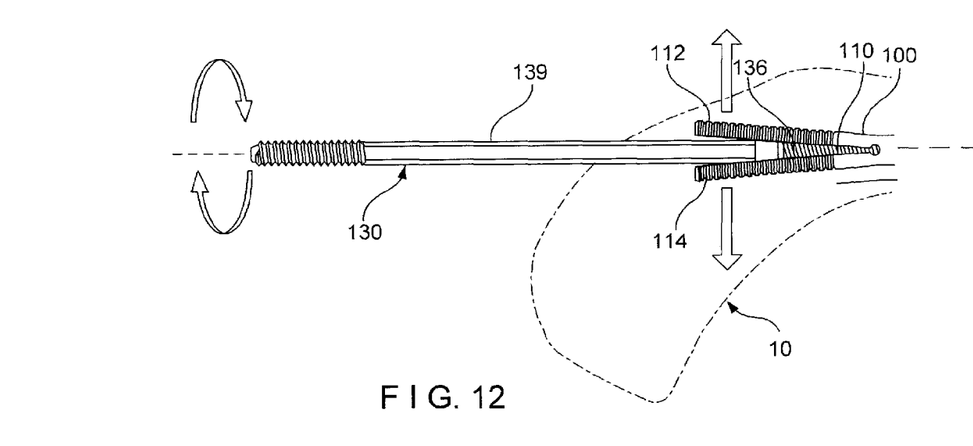
FIG. 12 illustrates the bone fixation device of FIG. 1 in the sixth operative configuration.
Figure 13:
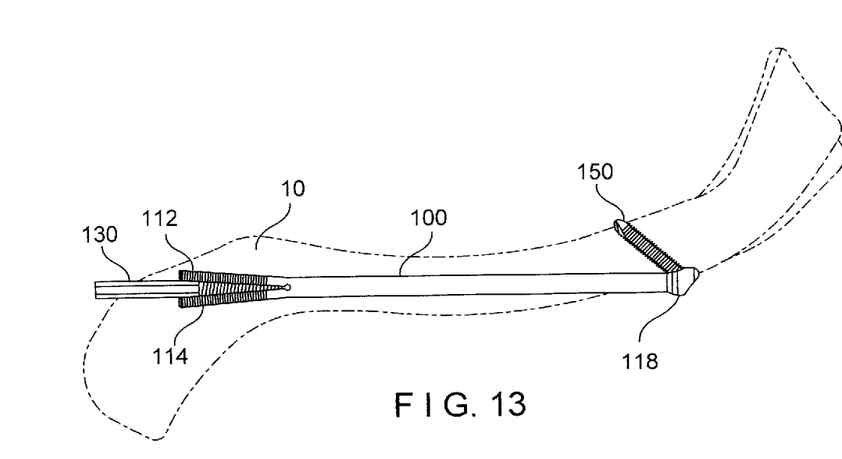
FIG. 13 illustrates the bone fixation device of FIG. 1 in a seventh operative configuration.

As shown in FIGS. 10-12, the expansion core 130 is then rotated relative to the device 100 so the male thread 136 advances further proximally into the female thread 116. Specifically, the expansion core 130 may be connected to an auxiliary instrument (not shown) to permit rotation thereof. In an exemplary embodiment, the auxiliary instrument (not shown) may be configured to engage the faceted body portion 139 of the expansion core. As the male thread is advanced, the expansion member 137 contacts and then causes the first and second wings 112, 114 to splay radially outward and frictionally engage an outer wall of an intramedullary canal of the clavicle 10. The expansion core 130 is rotated until engagement of the first end 132 with an end of the first and second slots 110, 111 prevents further rotation thereof. Once the first and second wings 112, 114 have been expanded to a desired position as shown in FIG. 12, the auxiliary instrument (not shown) may be removed from the expansion core 130. As shown in FIG. 13, a portion of the expansion core 130 extending distally from the clavicle 10 may then be trimmed so that a predetermined length thereof remains extending from the clavicle 10. The exemplary expansion core 130 according to the invention allows for the use of a standard length expansion core 130 and device 100 that permits a user to customize a length of the expansion core 130 to the requirements of a particular bone by clipping off an excessive length of the expansion core 130. In an exemplary embodiment, the portion of the expansion core 130 remaining external to the clavicle 10 after cutting may be approximately 5 mm. in length, although any other length is envisioned without deviating from the scope of the invention. As those skilled in the art will understand, the remaining portion of the expansion core 130 may be sized to facilitate gripping and removal thereof from the clavicle 10 after healing. In one embodiment, a predetermined length of the expansion core 130 may be formed with a smaller cross-section than outlying portions thereof to minimize the amount of force necessary to clip the expansion core 130. For example, a predetermined length of the expansion core 130 determined to be more likely to be positioned external to the clavicle 10 after implantation may be formed with the smaller cross-section. By leaving the expansion core 130 implanted in the clavicle 10, the first and second wings 112, 114 are prevented from moving radially inward due to stresses applied to the clavicle 10, as those skilled in the art will understand. Specifically, engagement of the first and second wings 112, 114 with the expansion member 137 of the expansion core 130 prevents a collapse thereof due to external stresses.

Once the clavicle 10 has healed, an incision is made adjacent to the medial end of the clavicle. The locking screw 150 is removed from the device 100 through the incision and an extraction tool or adaptor (not shown) is mounted to the trailing end 104 of the device 100. The extraction tool serves as an aid to maintain a position of the device 100 within the clavicle 10 as the expansion core 130 is being removed. A postero-lateral incision is then made adjacent to the protruding portion of the expansion core 130. The expansion core 130 is removed using a removal instrument that, for example, mates with the faceted body portion 139. Upon removal of the expansion core 130, the first and second wings 112, 114 may collapse or may be forced to collapse via withdrawal in a removal direction, such as in a direction from the leading end to the trailing end, using the extraction tool (not shown). The device 100 may then be withdrawn by applying a force to the extraction tool in the removal direction.

The exemplary method according to the invention avoids the need for an aiming device to guide insertion of the locking screw 150. Rather, since the transverse opening is open to an outer surface of the clavicle 10, the positioning accuracy of the locking screw 150 is independent of deflections of the device 100. The exemplary method of the invention requires only two incisions adjacent entry and exit points of the device relative to the bone, thus reducing patient trauma and simplifying the procedure. In another embodiment, three incisions may be formed if the bone is reduced using an open technique. In such cases, a third incision may be formed, for example, adjacent a fracture site, as those skilled in the art will understand.

Figures 14, 15:
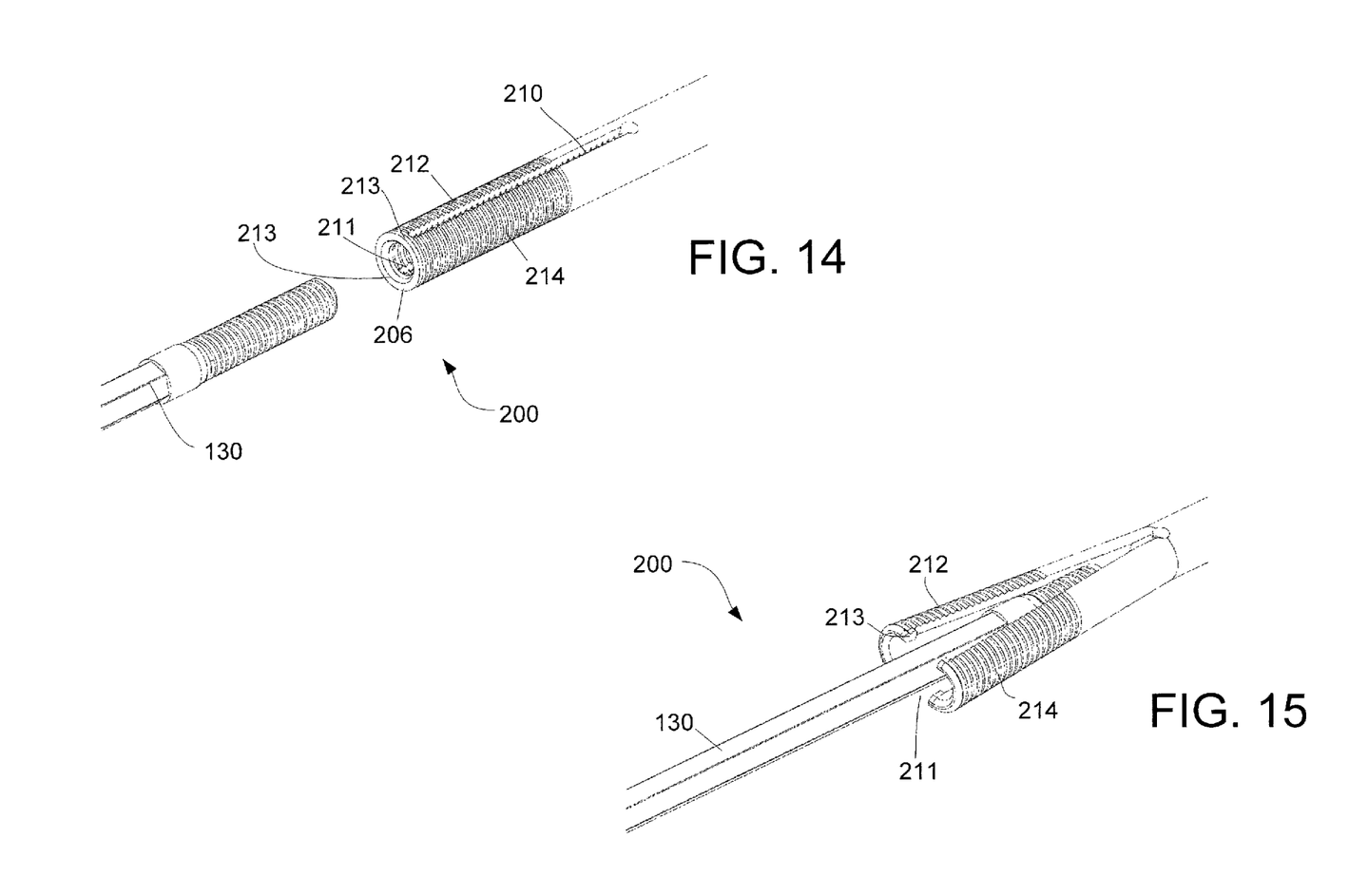
FIG. 14 illustrates a bone fixation device according to a first alternate embodiment of the invention in a first operative configuration.
FIG. 15 illustrates the bone fixation device of FIG. 14 in a second operative configuration.

FIGS. 14-15 depict a device 200 according to an alternate embodiment of the invention. The device 200 is formed substantially similarly to the device 100 of FIG. 1 with the exception of a construction of slots 210, 211 thereof. Specifically, the leading end 106 of the body 102 comprises first and second slots 210, 211 extending through opposing outer walls of the body 102 in a manner similar to the slots 110, 111 to define first and second wings 212, 214 on lateral sides thereof. In an exemplary embodiment, the slots 210, 211 do not extend to the leading end 106 but are separated therefrom by a predetermined distance. A breakable joint 213 is formed at the leading end 106 adjacent each of the slots 210, 211. In one exemplary embodiment, the joint 213 is approximately 0.5 mm. in length, although any other length may be employed without deviating from the scope of the invention. A length of the joint 213 is selected so that the joint 213 is broken when a predetermined force is applied thereto by the expansion core 130, as described in greater detail earlier. The exemplary embodiment of FIGS. 14-15 is configured to prevent a premature splaying to the wings 212, 214 during insertion into the bone, prior to the insertion of the expansion core 130 thereinto. Thus, once the body 102 has been inserted to a target position within the bone, advancement of the expansion core 130 into the leading end 106 of the body 102 applies a radial expansion force to the wings 212, 214 sufficient to cause a fracture of the joint 213 permitting the wings 212, 214 to splay outward, as described in greater detail earlier.

It will be apparent to those skilled in the art that various modifications and variations may be made in the structure and the methodology of the present invention, without departing from the spirit or scope of the invention. In one alternate embodiment, the body 102 may comprise any number of slots 110, 111 defining any plurality of wings. Thus, the exemplary embodiment of the present invention may be envisioned with any additional number of wings without deviating from the scope of the invention. Thus, it is intended that the present invention cover the modifications and variations of this invention provided that they come within the scope of the appended claims and their equivalents.

What is claimed is:

1. A bone fixation nail, comprising:
    an elongated body configured and dimensioned for insertion into a bone, the elongated body having a leading end and a trailing end, the elongated body including an internal thread on an inner wall thereof;
    a first slot extending through the elongated body from the leading end to a first point on the elongated body and defining first and second wings, the first and second wings configured to splay radially outward upon application of an internal stress thereto;
    an expansion device extending from a first end to a second end and having an engagement portion, the engagement portion having a first portion removably coupled in the first slot and a second portion configured and dimensioned to be engaged with the first slot to cause the first and second wings to splay radially outward, the first portion comprising a thread for engaging the internal thread of the elongated body; and
    a reamer configured to be coupled to the second end of the expansion device, the reamer being configured to drive the elongated nail body through a bone.

2. The bone fixation nail of claim 1, further comprising a transverse opening formed adjacent the trailing end, the transverse opening defining an insertion axis extending at an angle to a longitudinal axis of the elongated body and configured to receive a bone fixation element therethrough.

3. The bone fixation nail of claim 1, wherein the internal thread extends from the leading end of the elongated body to a second point on the elongated body, wherein the second point is located adjacent to the first point or closer to the trailing end than the first point.

4. The bone fixation nail of claim 1, wherein the second portion comprises an expander for splaying the first and second wings radially outwards.

5. The bone fixation nail of claim 4, wherein the first portion is adjacent the first end and comprises a thread for removably coupling the expansion device to the first slot and the second portion is adjacent to the first portion and comprises a tapered expander for causing the first and second wings to splay radially outward.

6. The bone fixation device of claim 1, wherein the first and second portions are the same portion and define a substantially conical thread, an outer diameter of a trailing end of the substantially conical thread being greater than an inner diameter of an internal thread in the first slot.

7. The bone fixation nail of claim 1, further comprising a gripping surface adjacent a leading end of the elongated body, wherein the gripping surface is an externally ribbed portion.

8. The bone fixation nail of claim 1, further comprising a second slot extending through the elongated body and extending from the leading end of the elongated body towards the trailing end, wherein the second slot extends through a portion of the elongated body different the portion through which the first slot extends.

9. The bone fixation nail of claim 1, further comprising a breakable joint adjacent a leading end of the first slot, the breakable joint configured to removably connect the first and second wings to one another.

10. A system for bone fixation, comprising:
    a bone fixation nail having an elongated body configured and dimensioned for insertion into a bone, the elongated body having a leading end and a trailing end, and a first slot extending through the elongated body from the leading end to a first point on the elongated body, the first slot defining first and second wings, the first and second wings being configured to splay radially outward upon application of an internal stress thereto;

an expansion device extending from a first end to a second end and having a engagement portion on a first end thereof, the engagement portion being configured and dimensioned to engage the first slot and to cause the first and second wings to splay radially outward; and a reamer configured to be connected the second end of the expansion device, the reamer being configured to drive the elongated nail body through a bone, wherein an internal thread is provided on an inner wall of the elongated body, and the engagement portion comprises a thread for engaging the internal thread.

11. The system of claim 10, further comprising a gripping portion defined on at least a portion of one of the wings.

12. The system of claim 10, wherein a portion of an outer body of the expansion device is faceted.

13. The system of claim 10, further comprising a second slot extending through the elongated body and extending from the leading end of the elongated body towards the trailing end, wherein the second slot extends through a portion of the elongated body different the portion through which the first slot extends.

14. The system of claim 1, further comprising a breakable joint adjacent a leading end of the first slot, the breakable joint configured to removably connect the first and second wings to one another.

15. A method for bone fixation, comprising the steps of:

inserting a leading end of a reamer into a first portion of a bone and guiding the reamer through the bone until the leading end exits a second portion of the bone;

pulling the leading end of the reamer to pull a bone fixation nail into the bone and guiding the bone fixation nail into a target position within the bone, the bone fixation nail having an expandable region to which an expansion device is connected in a first position; and expanding the expandable region by moving the expansion device to a second position different to the first position.

16. The method of claim 15, further comprising the step of:

threadedly attaching an expansion device to the expandable region before the reamer is pulled.

17. The method of claim 15, further comprising the step of inserting a locking screw into a transverse opening of the bone fixation device, wherein the transverse opening is located in an end of the bone fixation nail opposed to the end comprising the expandable region.

18. The method of claim 15, further comprising the step of rotating the expansion device relative to the bone fixation nail to move the expansion device to the second position; wherein the rotation causes a threaded portion of the expansion device to move further along an internal thread in the expandable region to cause the expandable region to expand.

19. The method of claim 15, wherein the expandable region has first and second wings that splay radially outward to lock an end of the bone fixation device within the bone.

20. The method of claim 15, further comprising the step of fracturing a joint connecting leading ends of the first and second wings to one another.

* * * * *